United States Patent [19]

Rindone et al.

[11] Patent Number: 5,220,039
[45] Date of Patent: Jun. 15, 1993

[54] ENERGETIC AZIDE PLASTICIZER

[75] Inventors: Renato R. Rindone, Fair Oaks; Der-Shing Huang, Carmichael; Edward E. Hamel, Roseville, all of Calif.

[73] Assignee: Aerojet General Corporation, Rancho Cordova, Calif.

[21] Appl. No.: 320,142

[22] Filed: Mar. 7, 1989

[51] Int. Cl.$^5$ .......................................... C07C 245/24
[52] U.S. Cl. ........................................ 552/11; 552/10
[58] Field of Search .................................. 552/10, 11

[56] References Cited

U.S. PATENT DOCUMENTS

| | | | |
|---|---|---|---|
| 3,291,833 | 12/1966 | Gold et al. | 260/584 |
| 3,523,808 | 8/1970 | Gold et al. | 106/287 |
| 3,526,667 | 9/1970 | Hill et al. | 260/615 |
| 4,406,718 | 9/1983 | Frankel et al. | 149/96 |

FOREIGN PATENT DOCUMENTS 1150059  6/1963  Fed. Rep. of Germany ........ 552/10

OTHER PUBLICATIONS

Chem Abstracts, vol. 110, No. 11; 94798f (1989).
Walker, J. F., and Chadwick, A. F., "Trioxane as a Source of Formaldehyde," Industrial and Engineering Chem., 39, 974–77, 1947.
Chemical Abstracts, vol. 67, 1967, 81778t, "Synthesis of Complex Halo Esters from α-Chloromethyl Esters of Carboxylic Acids".
Chemical Abstracts, vol. 96, 1982, p. 142, 96:165045p, "Tetraazido Polyesters".

Primary Examiner—Mary C. Lee
Assistant Examiner—J. Richter
Attorney, Agent, or Firm—Townsend and Townsend Khourie and Crew

[57] ABSTRACT

Novel multi-azido formals, acetals and ketals are disclosed, having the following generic formula

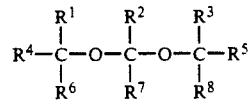

in which $R^1$, $R^2$, $R^3$, $R^4$, $R^5$, $R^6$, $R^7$ and $R^8$ are independently selected from H, $CH_3$, and $CH_2N_3$, and methods of preparation of these compounds.

18 Claims, No Drawings

ENERGETIC AZIDE PLASTICIZER

BACKGROUND AND SUMMARY OF THE INVENTION

This invention relates to novel chemical compounds used as plasticizers in polymeric formulations. In particular, this invention relates to novel, energetic, methylazide-substituted formals, acetals and ketals. These compounds have utility as energetic plasticizers for rocket and gun propellant and explosive formulations. A process for their preparation is also presented, as well as energetic compositions which include the novel plasticizers.

Solid propellants, such as those used for rocket propellants, are prepared by combining a variety of materials consisting of oxidizers binders plasticizers and a curing agent to solidify the formulation. The plasticizers may be either energetic or non-energetic in nature. Energetic plasticizers tend to be somewhat viscous in nature, and this limits the amount of solids that can be included in propellant formulations while maintaining good propellant processibility. Reducing the solids loading of a propellant generally results in a lowered propellant impulse.

This invention relates to a novel class of methylazide substituted acetals, formals and ketals for use as plasticizers in propellant systems, many of which are capable of being prepared from readily available starting materials, and to a novel process for their preparation.

This invention also resides in energetic compositions which include the methylazide-substituted acetals, formals and ketals as plasticizers. Such compositions have the combined benefits of improved propellant performance due to the energetic nature of the plasticizer, high solids loading and ease of processibility of the propellant formulation. The term "energetic compositions" is intended to include rocket and gun propellant and explosive formulations.

DETAILED DESCRIPTION OF THE INVENTION

The novel methylazide-substituted acetal, formal and ketal compounds of the present invention are represented by the formula:

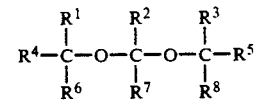

wherein $R^1$, $R^2$, $R^3$, $R^4$, $R^5$, $R^6$, $R^7$ and $R^8$ are independently selected from the group consisting of H, $CH_3$, and $CH_2N_3$, such that the total number of azide ($N_3$) groups is at least one. The term "independently selected" is used herein to indicate that two or more of the R groups may be identical.

Examples of acetals within the above formula are those in which $R^1$, $R^2$, $R^3$, $R^4$, $R^5$, $R^6$, $R^7$ and $R^8$ are as follows:

| $R^1$ | $R^2$ | $R^3$ | $R^4$ | $R^5$ | $R^6$ | $R^7$ | $R^8$ |
|---|---|---|---|---|---|---|---|
| H | H | H | $CH_2N_3$ | $CH_2N_3$ | $CH_2N_3$ | H | $CH_2N_3$ |
| H | H | H | $CH_3$ | $CH_3$ | $CH_2N_3$ | H | $CH_2N_3$ |
| H | $CH_3$ | H | $CH_2N_3$ | $CH_2N_3$ | $CH_2N_3$ | H | $CH_2N_3$ |
| H | $CH_3$ | H | $CH_3$ | $CH_3$ | $CH_2N_3$ | H | $CH_2N_3$ |
| H | $CH_2N_3$ | H | $CH_2N_3$ | $CH_3$ | $CH_2N_3$ | H | $CH_2N_3$ |
| H | $CH_2N_3$ | H | $CH_3$ | $CH_3$ | $CH_2N_3$ | H | $CH_2N_3$ |
| H | $CH_3$ | H | $CH_2N_3$ | $CH_2N_3$ | $CH_2N_3$ | $CH_3$ | $CH_2N_3$ |
| H | $CH_3$ | H | $CH_3$ | $CH_3$ | $CH_2N_3$ | $CH_3$ | $CH_2N_3$ |
| H | $CH_2N_3$ | H | $CH_2N_3$ | $CH_2N_3$ | $CH_2N_3$ | $CH_2N_3$ | $CH_2N_3$ |
| H | $CH_2N_3$ | H | $CH_3$ | $CH_3$ | $CH_2N_3$ | $CH_2N_3$ | $CH_2N_3$ |
| $CH_3$ | H | $CH_3$ | $CH_2N_3$ | $CH_2N_3$ | $CH_2N_3$ | H | $CH_2N_3$ |
| $CH_3$ | H | $CH_3$ | $CH_3$ | $CH_3$ | $CH_2N_3$ | H | $CH_2N_3$ |
| $CH_3$ | $CH_3$ | $CH_3$ | $CH_2N_3$ | $CH_2N_3$ | $CH_2N_3$ | H | $CH_2N_3$ |
| $CH_3$ | $CH_3$ | $CH_3$ | $CH_3$ | $CH_3$ | $CH_2N_3$ | H | $CH_2N_3$ |
| $CH_3$ | $CH_2N_3$ | $CH_3$ | $CH_2N_3$ | $CH_2N_3$ | $CH_2N_3$ | H | $CH_2N_3$ |
| $CH_3$ | $CH_2N_3$ | $CH_3$ | $CH_3$ | $CH_3$ | $CH_2N_3$ | H | $CH_2N_3$ |
| $CH_3$ | $CH_3$ | $CH_3$ | $CH_2N_3$ | $CH_3$ | $CH_2N_3$ | $CH_3$ | $CH_2N_3$ |
| $CH_3$ | $CH_3$ | $CH_3$ | $CH_3$ | $CH_3$ | $CH_2N_3$ | $CH_3$ | $CH_2N_3$ |
| $CH_3$ | $CH_2N_3$ | $CH_3$ | $CH_2N_3$ | $CH_2N_3$ | $CH_2N_3$ | $CH_2N_3$ | $CH_2N_3$ |
| $CH_3$ | $CH_2N_3$ | $CH_3$ | $CH_3$ | $CH_3$ | $CH_2N_3$ | $CH_2N_3$ | $CH_2N_3$ |
| $CH_2N_3$ | H | $CH_2N_3$ | $CH_2N_3$ | $CH_2N_3$ | $CH_2N_3$ | H | $CH_2N_3$ |
| $CH_2N_3$ | H | $CH_2N_3$ | $CH_3$ | $CH_3$ | $CH_2N_3$ | H | $CH_2N_3$ |
| $CH_2N_3$ | $CH_3$ | $CH_2N_3$ | $CH_2N_3$ | $CH_2N_3$ | $CH_2N_3$ | H | $CH_2N_3$ |
| $CH_2N_3$ | $CH_3$ | $CH_2N_3$ | $CH_3$ | $CH_3$ | $CH_2N_3$ | H | $CH_2N_3$ |
| $CH_2N_3$ | $CH_2N_3$ | $CH_2N_3$ | $CH_2N_3$ | $CH_2N_3$ | $CH_2N_3$ | H | $CH_2N_3$ |
| $CH_2N_3$ | $CH_2N_3$ | $CH_2N_3$ | $CH_3$ | $CH_3$ | $CH_2N_3$ | H | $CH_2N_3$ |
| $CH_2N_3$ | $CH_3$ | $CH_2N_3$ | $CH_2N_3$ | $CH_2N_3$ | $CH_2N_3$ | $CH_3$ | $CH_2N_3$ |
| $CH_2N_3$ | $CH_3$ | $CH_2N_3$ | $CH_3$ | $CH_3$ | $CH_2N_3$ | $CH_3$ | $CH_2N_3$ |
| $CH_2N_3$ | $CH_2N_3$ | $CH_2N_3$ | $CH_2N_3$ | $CH_2N_3$ | $CH_2N_3$ | $CH_2N_3$ | $CH_2N_3$ |
| $CH_2N_3$ | $CH_2N_3$ | $CH_2N_3$ | $CH_3$ | $CH_3$ | $CH_2N_3$ | $CH_2N_3$ | $CH_2N_3$ |

Within the scope of the above formula, certain embodiments are preferred, namely those in which $R^1$, $R^2$, $R^3$, $R^4$, $R^5$, $R^6$, $R^7$, and $R^8$ are independently H or $CH_2N_3$; those in which the total number of azide groups is at least two, preferably at least three, and most preferably at least four; those in which $R^6$ and $R^8$ are each $CH_2N_3$; those in which $R^2$ and $R^7$ are each $CH_2N_3$; those in which $R^4$, $R^5$, $R^6$, and $R^8$ are each $CH_2N_3$; and those in which $R^1$, $R^2$, $R^3$, $R^6$, $R^7$, and $R^8$ are each $CH_2N_3$.

The compounds of the invention may be symmetrical or asymmetric. Symmetrical compounds are preferred, i.e., those in which $R^1$ and $R^3$ are identical, $R^4$ and $R^5$ are identical, and $R^6$ and $R^8$ are identical.

The symmetrical compounds may be prepared by reacting a substituted alcohol with an aldehyde or ketone (or suitable oligomers such as trioxane) to form either a formal, an acetal or a ketal. The aldehyde or the ketone may or may not be substituted. The substitutions on the alcohol, aldehyde or ketone may consist of an azide group or any functional group that can be replaced by an azide group. Examples of the latter are halides such as chloride. In a typical reaction scheme, a halogen-substituted aliphatic alcohol is first reacted with a compound having an aldehyde or ketone functionality in the presence of a catalyst. This forms a formal (if formaldehyde is used), an acetal (if acetaldehyde is used) or a ketal (if a ketone is used), which is then reacted with a metal azide in a solvent to give the corresponding azide plasticizers. Examples of compounds having aldehyde or ketone functionalities are 1,3,5-trioxane, acetaldehyde, chloroacetaldehyde, acetone, and 1,3-dichloroacetone. Reactions of the alcohols with these compounds preferably take place at −5° C. to 35° C. in the presence of a catalyst, and are capable of producing yields above 95%. In preferred embodiments, however, the reactions are conducted at 15° C. to 25° C. with yields ranging from 75% to 85%. The reaction between the formal, acetal or ketal and the metal azide is preferably performed at 70° C. to 120° C. with yields ranging from 50% to 99%. Particularly preferred reactions are those involving the use of sodium azide at 75° C. to 100° C. with dimethyl sulfoxide as the solvent, whereupon yields of 95% to 99.9% may be obtained.

The asymmetrical compounds may be prepared by using a combination of alcohols rather than a single alcohol, then isolating the desired species from the product mixture using conventional purification techniques well known to those skilled in the art. Alternatively, the product mixture may itself be used without isolating single species.

The following example is intended to illustrate the invention and is in no way to be considered as a limitation on the inventive concept.

EXAMPLE

1. Preparation of bis(1,3-dichloro-2-propyl) formal

A three-neck 500-mL flask equipped with a thermometer, a mechanical stirrer, an addition funnel, a condenser, and a positive nitrogen atmosphere were charged with 1,3-dichloro-2-propanol (51.6 g, 0.4 mole), trioxane (6.0 g, 0.2 mole as formaldehyde), and 1,2-dichloroethane (200 mL). The mixture was a clear yellow solution. Concentrated sulfuric acid (29.8 g, 0.29 mole) was then added dropwise over sixteen minutes. During the addition, a slight exotherm was observed, and the flask was immersed in a water bath to maintain the reaction temperature at 16°–25° C. Once the addition was complete, the water bath was removed and the reaction mixture was stirred at 18°–22.5° C. for 2.7 hours. The agitator was then turned off. The lower (acid) layer (weighing 28.62 g) was removed, washed once with 50 mL 1,2-dichloroethane, and discarded. The 1,2-dichloroethane layers were then combined and washed with two 300-mL portions of 1% aqueous NaHCO$_3$, followed by two 300-mL portions of deionized water. The solution was then stripped in vacuo leaving a yellow liquid, weighing 43.32 g (80.2% yield) which solidified into a slush-like consistency upon standing at ambient temperature. The product was identified as bis(1,3-dichloro-2-propyl) formal by proton nuclear magnetic resonance (NMR) (CDCl$_3$) δ 4.8 (s, —OCH$_2$O—), 4.0 (m, (ClCH$_2$)$_2$CHO—), 3.6 (d, (ClCH$_2$)$_2$CHO—).

2. Preparation of bis(1,3-diazido-2-propyl) formal (BDPF)

A three-neck 250-mL flask equipped with a mechanical stirrer thermometer, addition funnel, heating mantle and nitrogen atmosphere was charged with dimethyl sulfoxide (75 mL) and heated to 75° C. Sodium azide (5.05 g, 77.7 mmoles) was then added in one portion. The mixture was heated to 95° C. The product of part 1 above (5.0 g, 18.5 mmoles) dissolved in 25 mL of dimethylsulfoxide was then added dropwise over thirty-two minutes at 94.5°–99.2° C. Upon completion of the addition, stirring was continued for four hours at 95°–99° C. The mixture was then cooled to ambient temperature, quenched with 200 mL of deionized water, and extracted with two 100-mL portions of methylene chloride. The resulting aqueous solution was discarded, and the combined methylene chloride phases were washed with two 200-mL portions of water and stripped in vacuo to give a yellow oil, weighing 5.42 g (98.7% yield). The oil was identified as bis(1,3-diazido-2-propyl) formal by infrared analysis (film): 2950 cm$^{-1}$ (CH), 2125 cm$^{-1}$ (N$_3$), 1290 cm$^{-1}$, 1175 cm$^{-1}$, 1120 cm$^{-1}$, 1040 cm$^{-1}$ (OCH$_2$O); and proton NMR (CDCl$_3$) δ 4.8 (s, OCH$_2$O), 3.8 m, (N$_3$CH$_2$)$_2$CHO), 3.3 (d, (N$_3$CH$_2$)$_2$CHO).

Table 1 presents physical properties and analytical results of neat BDPF, Table 2 presents calculated thermodynamic properties, and Table 3 hazard properties of BDPF neat and in solvent solutions. In the hazard properties tests, neat BDPF and BDPF solvent solutions were subjected to a series of standard tests using industry-accepted test procedures. These included Bureau of Mines Impact tests, electric spark sensitivity tests, rotary friction tests, differential thermal analyses (DTA), differential scanning calorimetry (DSC), Naval Ordnance Laboratory (NOL) detonability (card gap) tests and unconfined burning tests.

TABLE 1

PHYSICAL PROPERTIES and ANALYTICAL RESULTS, NEAT BDPF

| | |
|---|---|
| Chemical structure: | (N$_3$CH$_2$)$_2$ CHOCH$_2$OCH (CH$_2$N$_3$)$_2$ |
| Molecular Formula: | C$_7$ H$_{12}$N$_{12}$O$_2$ |
| Molecular Weight: | 296.25 |
| Appearance: | Colorless liquid |
| Density: | (@ 21° C.): 1.29 gm/ml |
| Freezing Point: | −22° C. |
| Purity (GC area %): | |
| Methylene Chloride | 0.02 |
| Unknown Low Boilers | 1.19 |
| Bis(1,3-dichloro-2-propyl) formal (BDCPF) | 0.55 |
| BDPF | 86.03 |
| Polyoxymethylene Derivatives of BDPF | 12.21 |
| Total Chloride (wt. %): | 0.24 |
| Vacuum Stability (100° C., 48 hrs.), ml/gm: | 2.56; 2.58; 2.85 |

TABLE 2

THERMODYNAMIC PROPERTIES (calculated)

| | |
|---|---|
| Heat of formation, (kcal/mole) | +239.4 |
| Heat of combustion, (kcal/mole) | −1307.9 |

TABLE 3

HAZARD PROPERTIES OF BDPF SOLVENT SOLUTIONS

| Test | solvent: % BDPF: | 100 | CH$_2$Cl$_2$ 50 | 40 | 20 | DMSO 30 |
|---|---|---|---|---|---|---|
| Impact (cm at 2 kg) | | 42–46 | >100 | — | >100 | >100 |
| Spark sensitivity (joules) | | >1.0 | >1.0 | — | >1.0 | >1.0 |
| Rotary friction (g at 2000 rpm) | | 1000–1060 | >4000 | — | >4000 | >4000 |
| DTA (°C.) | | | | | | |
| exotherm onset | | 159 | 169 | — | 198 | 150 |
| exotherm peak | | 218 | 206 | — | 219 | 175, 188 |
| DSC (°C.) | | | | | | |
| exotherm onset | | 218 | — | — | — | — |
| exotherm peak | | 247 | — | — | — | — |
| NOL card gap using zero cards | | — | pos | neg | — | — |
| Unconfined burn of 100 mL sample (sec) | | — | — | — | — | 576 |

To those skilled in the art, many modifications and variations of the present invention are possible in light of the above teachings. It is therefore to be understood that the present invention may be practiced otherwise than as specifically described herein and still be within the spirit and scope of the appended claims.

What is claimed is:

1. A compound having the formula

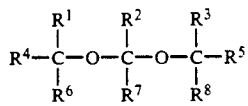

in which $R^1$, $R^2$, $R^3$, $R^4$, $R^5$, $R^6$, $R^7$, and $R^8$ are independently selected from the group consisting of H, CH$_3$, and CH$_2$N$_3$ such that the total number of azide groups is at least one.

2. A compound in accordance with claim 1 in which the total number of azide groups is at least two.

3. A compound in accordance with claim 1 in which the total number of azide groups is at least three.

4. A compound in accordance with claim 1 in which the total number of azide groups is at least four.

5. A compound in accordance with claim 1 in which the total number of azide groups is three.

6. A compound in accordance with claim 1 in which the total number of azide groups is four.

7. A compound in accordance with claim 1 in which the total number of azide groups is five.

8. A compound in accordance with claim 1 in which the total number of azide groups is six.

9. A compound in accordance with claim 1 in which the total number of azide groups is seven.

10. A compound in accordance with claim 1 in which the total number of azide groups is eight.

11. A compound in accordance with claim 1 in which $R^1$ and $R^3$ are identical, $R^4$ and $R^5$ are identical, and $R^6$ and $B^8$ are identical.

12. A compound in accordance with claim 1 in which $R^1$, $R^2$, $R^3$, $R^4$, $R^5$, $R^6$, $R^7$, and $R^8$ are independently selected from the group consisting of H and CH$_2$N$_3$.

13. A compound in accordance with claim 1 in which $R^6$ and $R^8$ are each CH$_2$N$_3$.

14. A compound in accordance with claim 1 in which $R^2$ and $R^7$ are each CH$_2$N$_3$.

15. A compound in accordance with claim 1 in which $R^4 R^5$, $R^6$ and $R^8$ are each CH$_2$N$_3$.

16. A compound in accordance with claim 1 in which $R^1$, $R^2$, $R^3$, $R^6$, $R^7$, and $R^8$ are each CH$_2$N$_3$.

17. A compound in accordance with claim 1 in which $R^4$, $R^5$, $R^6$, and $R^8$ are each CH$_2$N$_3$, and $R^1$, $R^2$, $R^3$ and $R^7$ are each H.

18. A compound in accordance with claim 1 in which $R^4$, $R^5$, $R^6$, and $R^8$ are each CH$_2$H$_3$; $R^1$, $R^2$, and $R^3$ are each H; and $R^7$ is CH$_3$.

* * * * *